United States Patent [19]

Knippscheer et al.

[11] Patent Number: 4,969,336
[45] Date of Patent: Nov. 13, 1990

[54] CRYOGENIC STORAGE APPARATUS, PARTICULARLY WITH AUTOMATIC RETRIEVAL

[75] Inventors: Hermann Knippscheer, Baldwin, N.Y.; Daniel D. Richard, Sedona, Ariz.

[73] Assignee: Cryo-Cell International, Inc., Beach Haven, N.J.

[21] Appl. No.: 389,543

[22] Filed: Aug. 4, 1989

[51] Int. Cl.$^5$ ............................................. F25D 23/02
[52] U.S. Cl. ...................................... 62/266; 62/337; 62/448
[58] Field of Search ................... 62/63, 265, 266, 374, 62/440, 448, 336, 337

[56] References Cited

U.S. PATENT DOCUMENTS

| | | | |
|---|---|---|---|
| 1,938,985 | 12/1933 | Starr | 312/268 |
| 2,599,173 | 6/1952 | Hamilton | 62/336 |
| 2,950,605 | 8/1960 | Hennion | 312/268 |
| 3,034,845 | 5/1962 | Haumann | 312/268 |
| 3,141,123 | 7/1964 | Olson | 312/268 |
| 3,583,171 | 6/1971 | Flynn et al. | 62/266 |
| 3,696,631 | 10/1972 | Valdes | 62/448 |
| 3,942,334 | 3/1976 | Pink | 62/266 |
| 4,340,263 | 7/1982 | Webb | 312/268 |

Primary Examiner—Ronald C. Capossela
Attorney, Agent, or Firm—R. Neil Sudol; Henry D. Coleman

[57] ABSTRACT

A cryogenic storage apparatus comprises a housing with an automatically operated access door. A holder device disposed in the housing supports a plurality of specimen-containing ampules, while a conveyor moves the holder device, together with the plurality of ampules, through cooling fluid in the housing along a path preferably including a snaking portion with vertically extending folds. An inverted L-shaped cooling component with an opened upper side is disposed in the housing for maintaining the cooling fluid at a predetermined low temperature. An extraction mechanism disposed outside of the housing at the access door serves to remove a selectable ampule positioned in the housing in juxtaposition to the door. A tracking device automatically tracks the positions of the ampules during motion thereof along the snaking path, while a control unit connected to the tracking device, the drive mechanism, the conveyor and the extraction mechanism activates the conveyor to move a given ampule along the path to the access door, opens the access door, and operates the extraction mechanism to remove the given ampule from the holder device and out through the opened door.

34 Claims, 12 Drawing Sheets

CRYOGENIC STORAGE APPARATUS, PARTICULARLY WITH AUTOMATIC RETRIEVAL

BACKGROUND OF THE INVENTION

This invention relates to a cryogenic storage apparatus. More particularly, this invention relates to an apparatus for the preservation of biological specimens at or near the temperature of liquid nitrogen.

When properly treated, biological specimens can be stored almost indefinitely at temperatures approaching that of liquid nitrogen so long as that temperature is maintained. However, once the temperature of a specimen is raised, especially to a level where thawing occurs, the integrity of the specimen suffers if the specimen is then refrozen. Conventional devices for storing biological specimens at low temperatures are adequate for the storage of a group of samples, but if one or more samples are removed from the group, other samples may be exposed to thawing temperatures, with a resultant decrease in the viability of the refrozen cells.

OBJECTS OF THE INVENTION

An object of the present invention is to provide a cryogenic storage apparatus for maintaining specimens at a substantially constant temperature at or near the temperature of liquid nitrogen.

Another object of the present invention is to provide such an apparatus wherein exposure of the specimens to temperatures above that of liquid nitrogen, especially thawing temperatures, is prevented.

Another, more particular, object of the present invention is to provide such an apparatus wherein individual specimencontaining vials may be recovered or retrieved either automatically or manually, while avoiding exposure of other vials to warm air.

A further particular object of the present invention is to provide such an apparatus for the storage of biological specimens, particularly including tissue samples, bone marrow, sperm cells, and carcinogenic cells, for installation in hospitals, laboratories and sperm or marrow banks.

Yet another particular object of the present invention is to provide such an apparatus wherein the coolant used is liquid nitrogen and the specimen-containing ampules or vials are not exposed to the liquid nitrogen.

Another object of the present invention is t provide such an apparatus wherein human intervention is limited to a minimum.

SUMMARY OF THE INVENTION

A cryogenic storage apparatus comprises, in accordance with the present invention, a housing defining a storage chamber for containing a cooling fluid, the housing having an access door provided with means operatively connected to the door for alternately opening and closing the door. A holder device is disposed in the chamber for supporting a plurality of specimencontaining receptacles, while a conveyor is provided in the chamber for moving the holder device together with the plurality of receptacles, through the fluid in the chamber along a path preferably including a snaking portion. The snaking portion of the path has a plurality of vertically extending folds and a segment juxtaposed to the door. A cooling component is disposed at least partially in the chamber for maintaining the cooling fluid (e.g., a gas such as nitrogen vapor) at a predetermined low temperature. An extraction mechanism is disposed outside of the housing at the door for removing a selectable one of the receptacles positioned in the chamber in juxtaposition to the door.

Preferably, the door is opened automatically, the means for opening the door comprising a drive mechanism.

Pursuant to another feature of the present invention, a tracking device is operatively connected to the conveyor mechanism for automatically tracking the positions of the plurality of receptacles during motion thereof along the path in response to the conveyor. In addition, a control unit is operatively connected to the tracking device, the drive mechanism, the conveyor and the extraction mechanism for operating the conveyor to move a given one of the receptacles along the path to the door, for operating the drive mechanism to open the door, and for operating the extraction mechanism to remove the given receptacle from the holder device and out through the opened door.

Pursuant to another feature of the present invention, the cooling component includes a coolant container having an L-shaped cross-section with a pair of hollow substantially planar leg members extending orthogonally with respect to one another. One of the leg members extends horizontally and proximately to an upper wall of the housing, while another of the leg members extends vertically and proximately to a side wall of the housing.

Preferably, the vertical leg member is formed with cooling fins disposed between the vertical leg member and the side wall of the housing. In addition, the horizontal leg member advantageously has an open upper side.

Pursuant to yet another feature of the present invention, an insulated enclosure is provided outside of the housing, the extraction mechanism operating to remove a selectable one of the receptacles positioned in the chamber in juxtaposition to the door and insert the removed receptacle into the enclosure.

In accordance with additional features of the present invention, a selector device is provided outside of the housing for enabling a selection of one of the receptacles by an operator, the control means operating in response to the selector device to remove a selected receptacle from the housing.

Preferably, the access door in the housing has a wedgeshaped cross-section and engages a sloped surface of the housing, the drive for alternately opening and closing the door including means for sliding the door along the surface. Also, the conveyor advantageously includes a pair of flexible endless elements extending along the path, the holder device including a plurality of bar members pivotably connected to and extending between the endless elements.

A cryogenic storage apparatus in accordance with the present invention maintains specimens at a substantially constant temperature at or near the temperature of liquid nitrogen. Exposure of the specimens to temperatures above that of liquid nitrogen, especially thawing temperatures, is prevented, insofar as individual specimen-containing vials may be inserted or retrieved either automatically or manually, while avoiding exposure of other vials to warm air.

Specimens are maintained at a substantially constant low temperature in part because the conveyor is driven slowly through the storage chamber.

An apparatus in accordance with the present invention is particularly adapted for the storage of biological specimens, particularly including tissue samples, bone marrow, sperm cells, and carcinogenic cells, for installation in hospitals, laboratories and sperm or marrow banks.

In one embodiment of the present invention, the coolant used is liquid nitrogen and the specimen-containing ampules or vials are not exposed to the liquid nitrogen.

In an apparatus in accordance with the present invention, human intervention is limited to a minimum. The apparatus serves the purposes of long term storing and computer controlled accessing of biological specimens.

DETAILED DESCRIPTION

Figure 1:
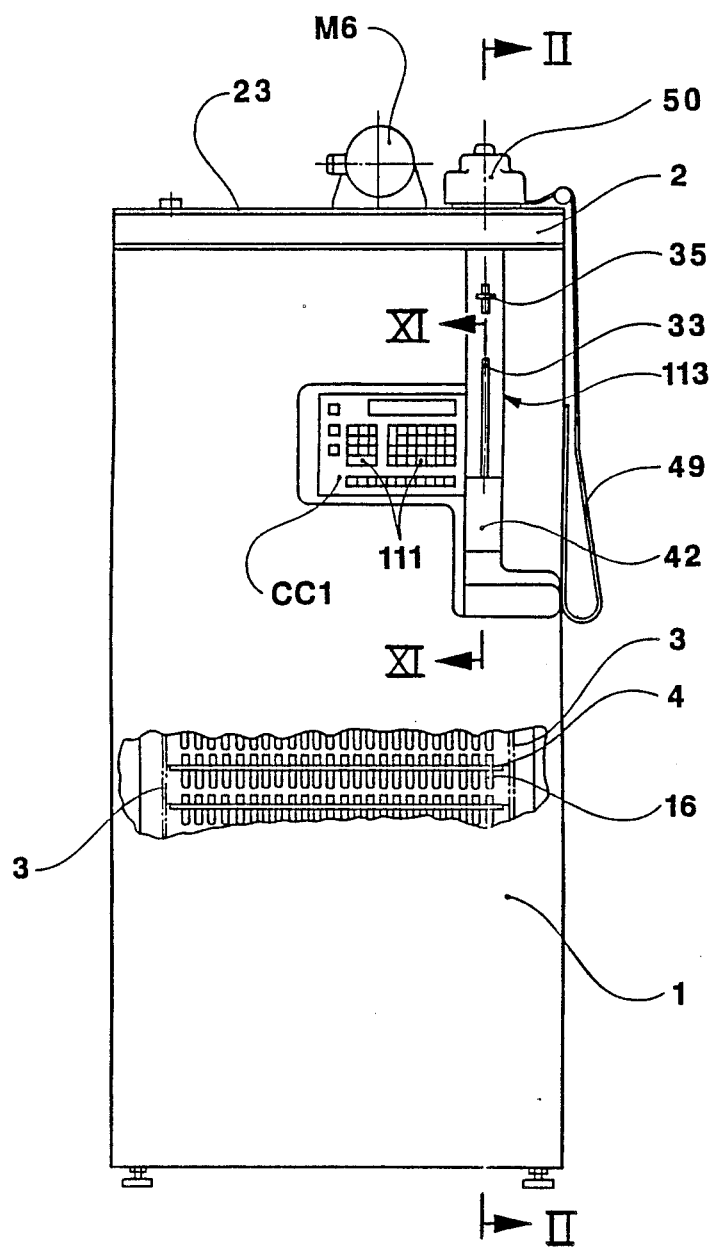
FIG. 1 is a front elevational view of a cryogenic storage apparatus in accordance with the present invention.
Figure 2:
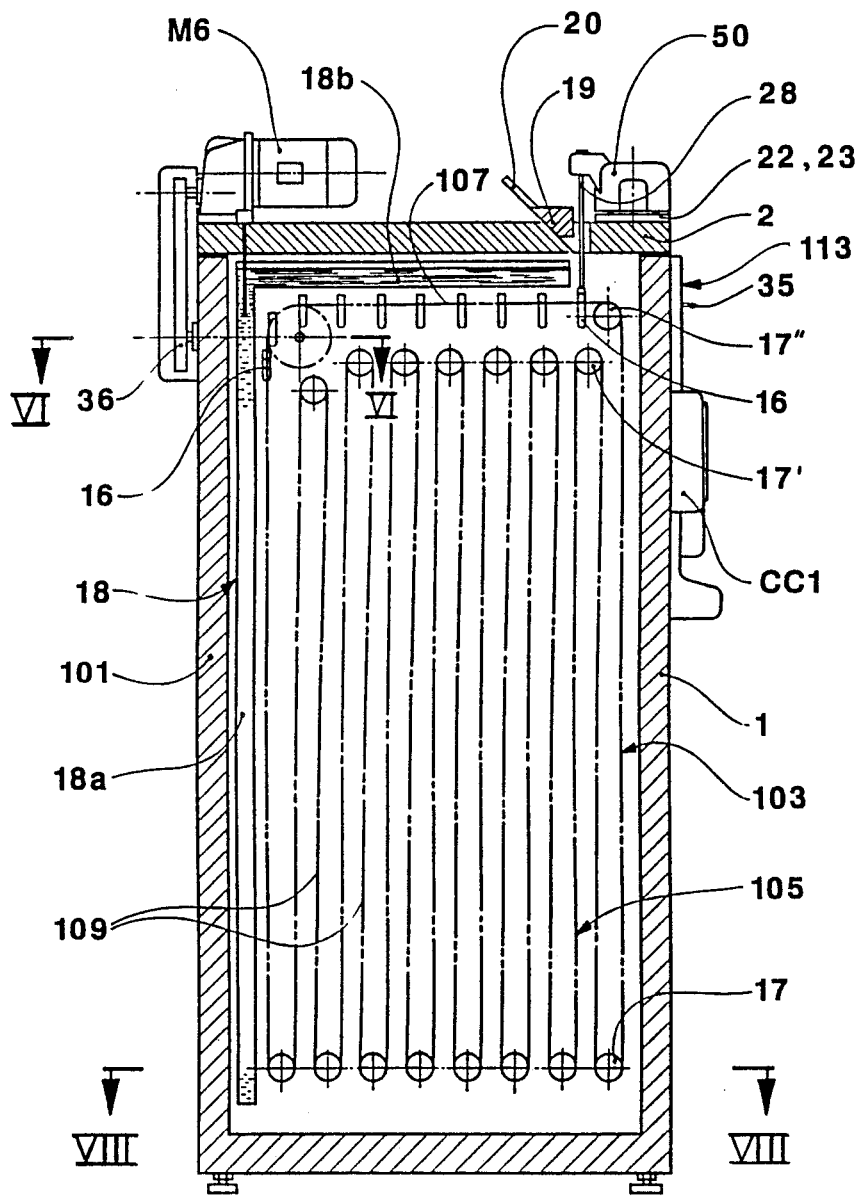
FIG. 2 is a schematic cross-sectional view taken along line A—A in FIG. 1.

As illustrated in FIGS. 1 and 2, a cryogenic storage apparatus for maintaining ampules or receptacles 16 at a substantially uniform low temperature approximately at the temperature of liquid nitrogen comprises a housing 1 with a lid or cover 2.

Ampules 16 are loaded into and retrieved from housing 1 automatically under the control of a microprocessor or computer CC1 mounted to housing 1 on a side wall thereof. The insertion and withdrawal of individual ampules is accomplished without exposure of the other specimen-containing ampules in housing 1 to ambient room-temperature air.

The cryogenic storage apparatus illustrated in FIGS. 1 and 2 will store approximately 8,000 ampules, each containing a respective specimen or sample.

Housing 1 defines a prismatic storage chamber which can be partially or totally filled with liquid nitrogen or a lowtemperature gas. In the latter case, the gas is maintained at a low temperature by a minimal amount of liquid nitrogen held in a specially designed container 18 (FIG. 2). Container 18 preferably has an L-shaped cross-section with vertically extending leg 18a and a horizontally oriented leg 18b communicating with one another. Vertical leg 18a extends parallel and proximate to a side wall 101 of housing 1, while horizontal leg 18b is disposed near cover or upper wall 2 of the housing. Vertical leg 18a is provided on one side with a multiplicity of cooling fins which may engage side wall 101, while horizontal leg 18b is open along an upper side. The shape and location of container 18 are designed to achieve a temperature balance within housing 1 by virtue of radiant and gravitational cooling.

Figure 3:
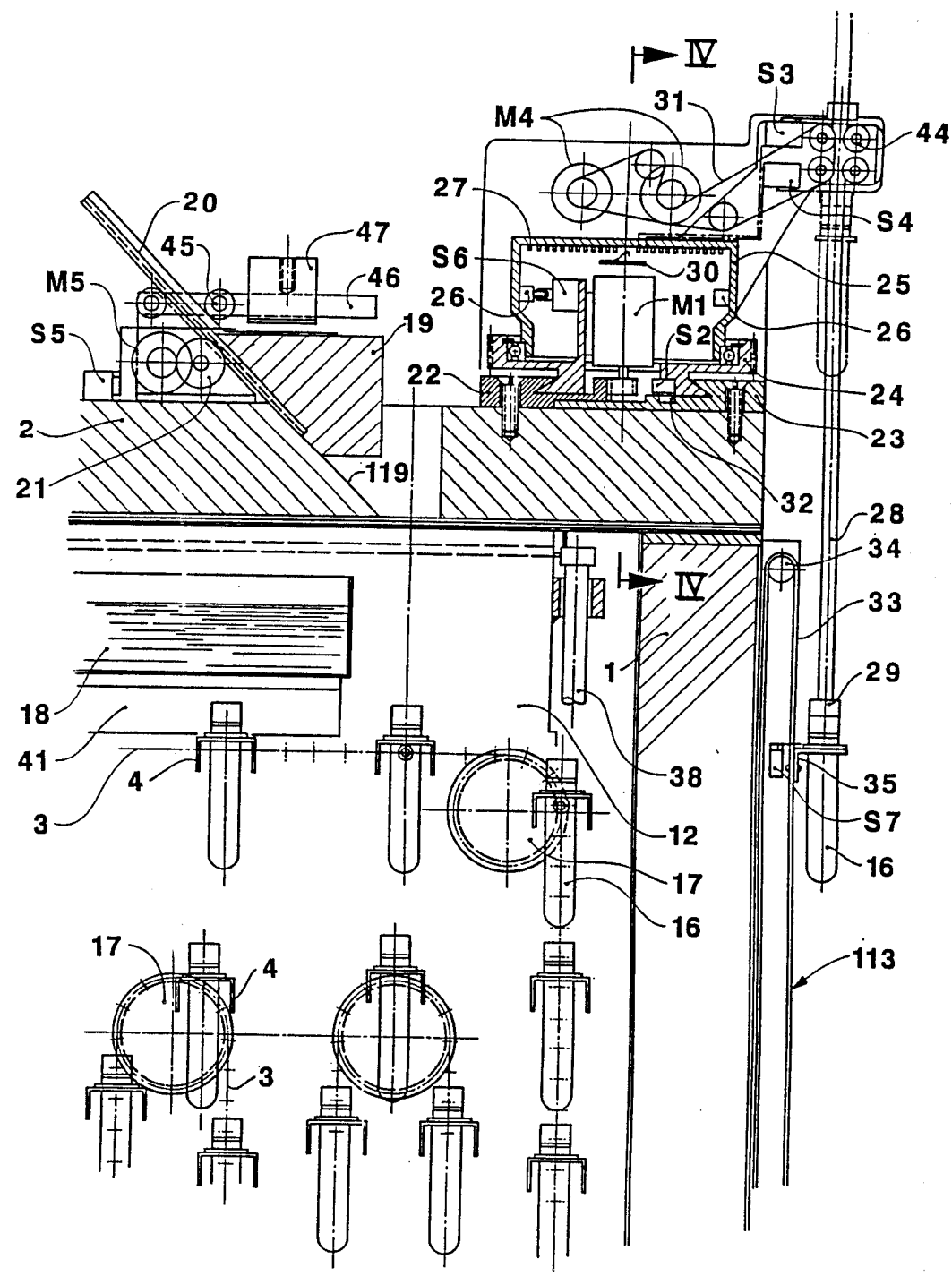
FIG. 3 is an enlarged, detail view ("Detail A") of the upper right hand corner of FIG. 2.

As shown in FIGS. 1 and 3, pluralities of ampules 16 are held on respective support bars 4 extending between and pivotably connected at their ends to a pair of endless conveyor chains 3. As shown in FIG. 2, chains 3 define a travel path 103 for the ampules through the housing chamber, the travel path having a lower snaking portion 105 and an upper portion 107 extending horizontally parallel to cover 2. Snaking portion 105 includes a plurality of vertically extending folds 109.

The position of each ampule 16 along path 103 is tracked in part by computer CC1. The computer memorizes the positions of all the ampules and updates the positions continuously during the motion of conveyor chains 3. In response to a selection made by an operator via a keyboard 111 (FIG. 1) of computer CC1, the computer controls the movement of chains 3 to position the selected ampule directly below an access door 19 in cover 2 (see FIGS. 2 and 3).

The snake-like alternating up and down movements of bars 4 and ampules 16 supported thereby contributes to the achievement of a gravitational temperature balance throughout the storage unit, in the case that coolant container 18 is being utilized.

The processes and devices for storing the liquid nitrogen outside housing 1, feeding it to container 18 and insulating housing 1 are well known in the art and are not further described herein.

The material of housing 1, container 18 and other components of the cryogenic storage apparatus in accordance with the present invention, if not specifically set forth elsewhere herein, is preferably stainless steel or another substance suitable for long-term exposure to liquid nitrogen.

As illustrated in FIGS. 1-3, 11 and 12, the cryogenic storage apparatus is provided with an ampule lifting device 113 comprising a conveyor belt 33, pulleys 34 and motors M3 and their supports. The lifting device is particularly advantageous in the case that the height of housing 1 is so great that the ampule, when resting with an insulated enclosure or intermediate storage unit 142, is not easily accessible by an ampule insertion and extraction or retrieval mechanism 50 disposed on cover 2.

Motors M1 through M5 are duplex drives, each working motor being paired with an auxiliary back-up motor as a safety or precautionary measure. In the event that a primary, working motor should fail, the auxiliary motor will take over automatically and an audio visual signal will be generated, alerting an operator to initiate immediate maintenance and repair procedures.

Figure 5:
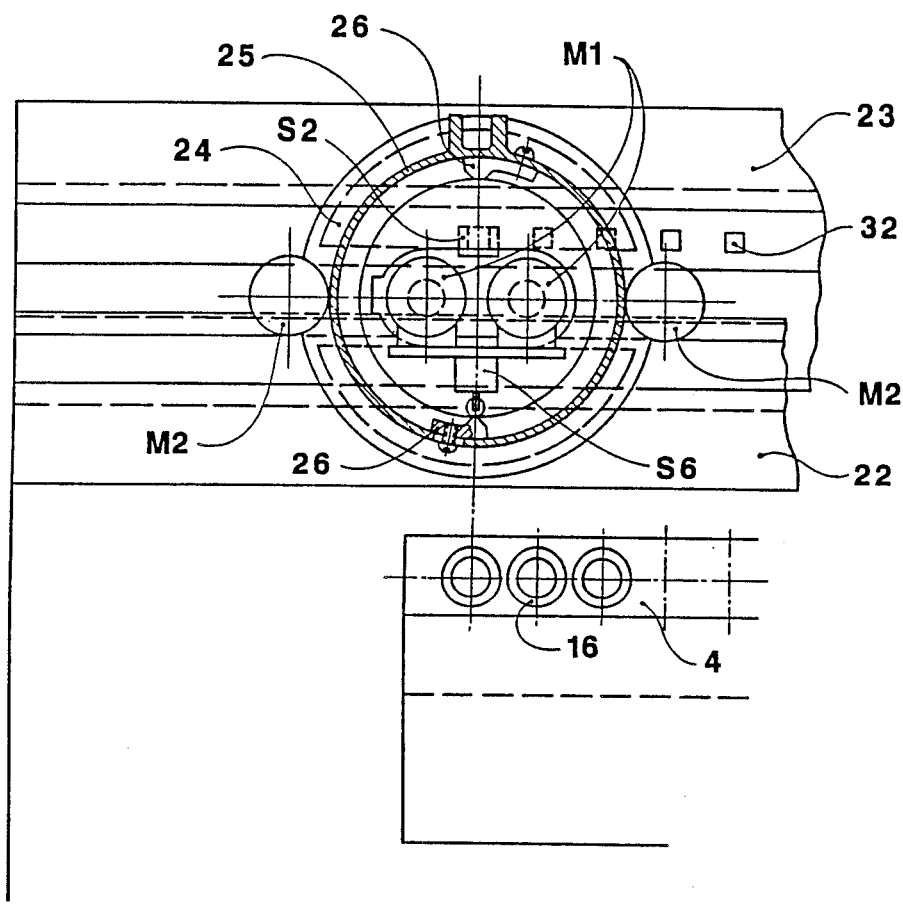
FIG. 5 is a partial cross-sectional view taken along line C—C in FIG. 4.

As illustrated in FIG. 3, support bars 4 have U-shaped transverse cross-sections. As best seen in FIGS. 1, 5 and 7, ampules 16 rest side by side on bars 4. Endless conveyor chains 3 are driven by a chain drive mechanism 115 (FIGS. 6 and 7) including sprockets 5 (FIG. 6) and 6 (FIG. 7) over idler pulleys 17 (FIGS. 3, 8 and 9) absolutely simultaneously along path 103 at a very low speed through the housing chamber. Bars 4 are fastened to chains 3 at spaced locations distanced to enable a free movement and vertical self-alignment of the bars and the ampules held thereby.

Figure 6:
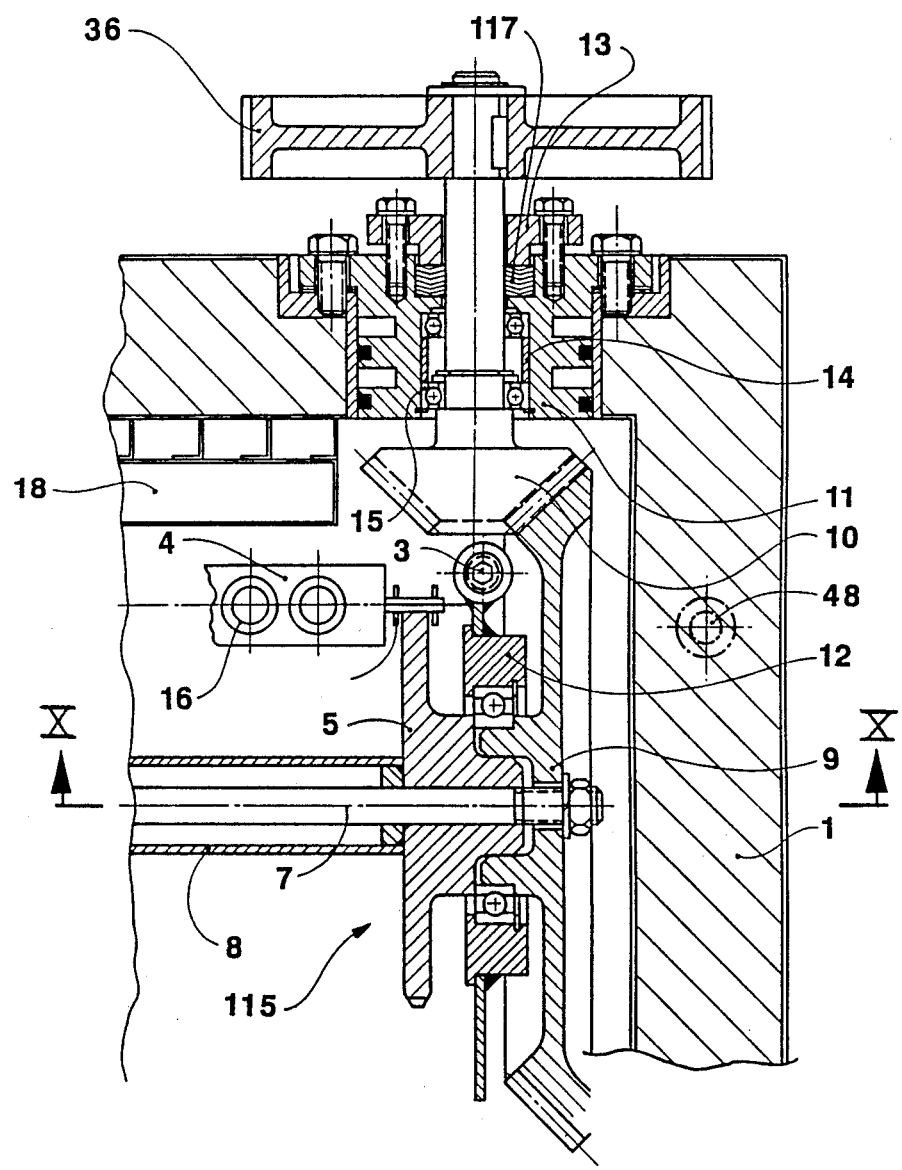
FIG. 6 is a cross-sectional view taken along line D—D in FIG. 2, showing a chain drive gear assembly.
Figure 7:
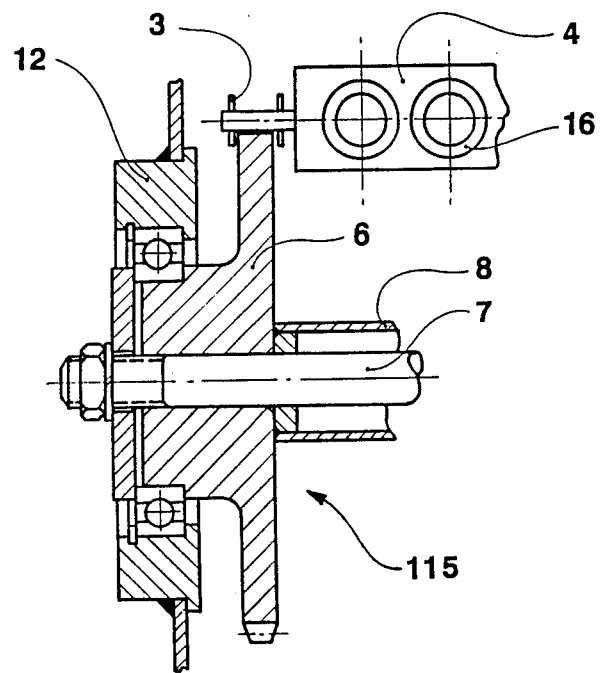
FIG. 7 is a cross-sectional view of a driving gear opposite a gear shown in FIG. 6.
Figure 10:
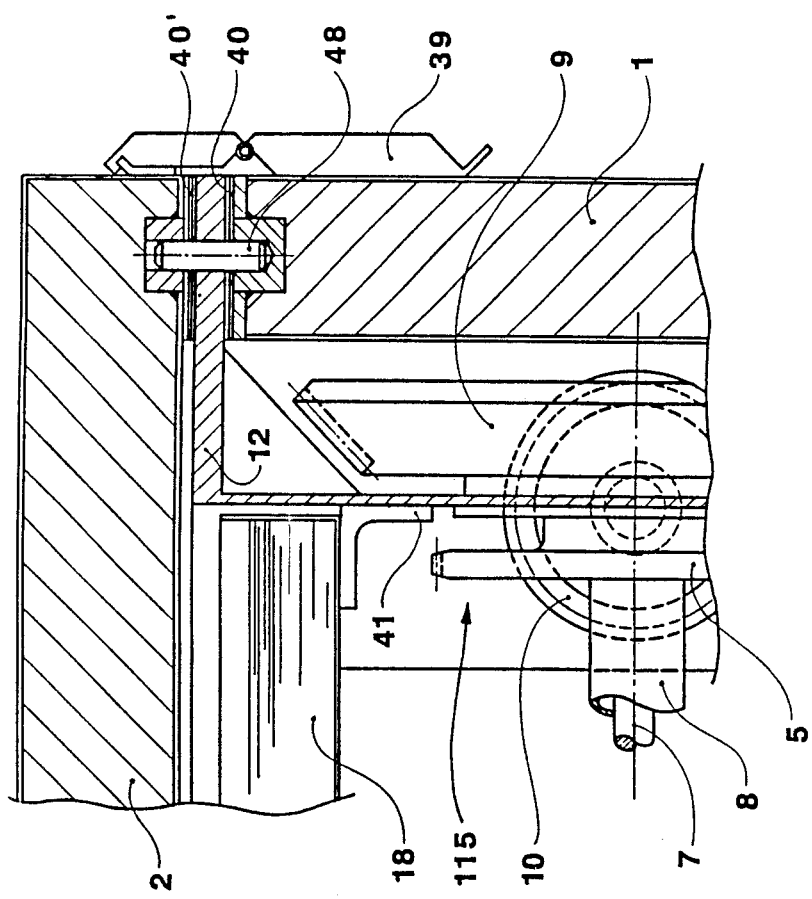
FIG. 10 is a partial cross-sectional view taken along line H—H in FIG. 6.

As depicted in FIGS. 6, 7 and 10, sprockets 5 and 6 of chain drive mechanism 115 are tightened against a spacer 8 by a spindle 7 and are driven by bevel gears 9 and 10. Bevel gear 10 is rotatably supported via roller bearings 15 and a distance sleeve 14 in a bearing casing 11. Driving mechanism 115 is sealed by a stuffing box 13 with graphite packing 117. The bevel gear assembly illustrated in FIG. 6 is designed to be removed and maintained easily and quickly.

Bevel gears 9 and 10 of driving mechanism 115 are powered by a motor M6 disposed on the top and rear portion of cover 2. Motor M6 is operatively connected to bevel gears 9 and 10 via a toothed belt drive 36 (FIGS. 2 and 6).

Figure 8:
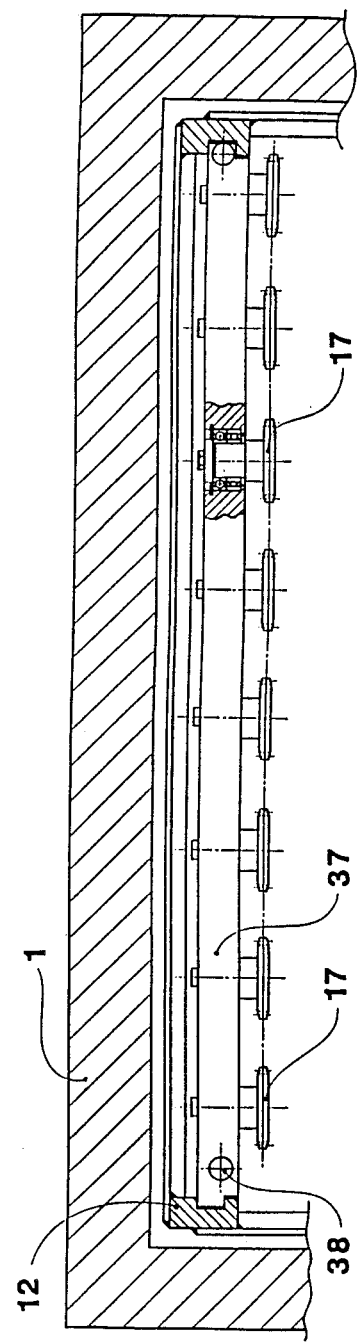
FIG. 8 is a partial cross-sectional view taken along line E—E in FIG. 2, illustrating a chain tensioning mechanism.
Figure 9:
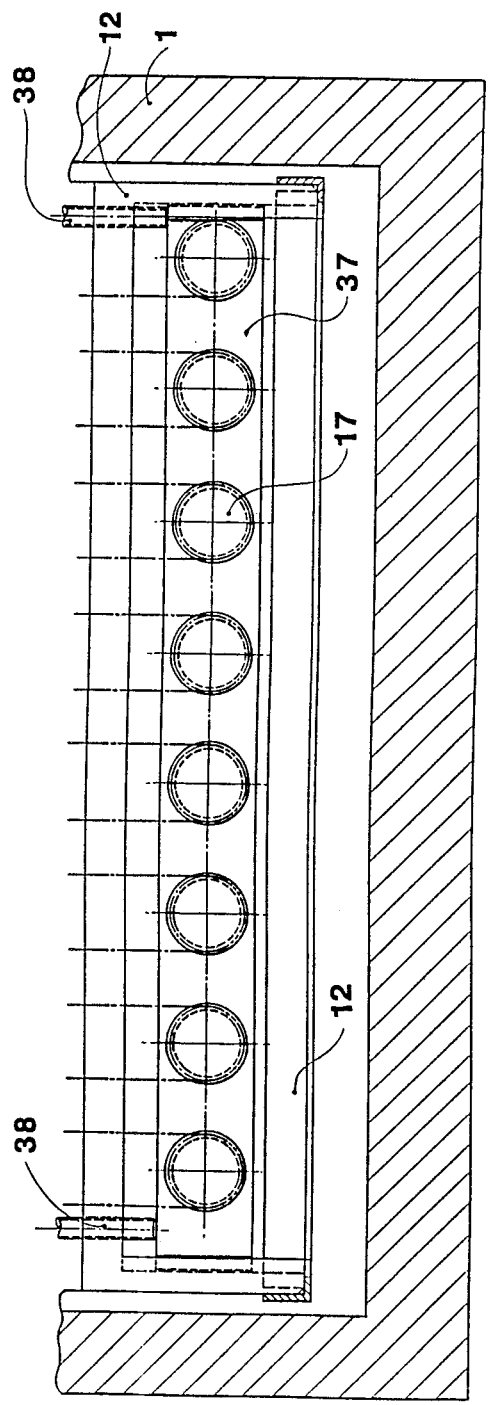
FIG. 9 is an elevational view of the chain tensioning mechanism of FIG. 8, taken from the bottom in that drawing figure and, as in FIG. 8, showing in cross-section a portion of a housing of the cryogenic storage apparatus.

As illustrated in FIGS. 2, 8 and 9, each endless conveyor chain 3 is partially wound over idler pulleys 17 and 17' rotatably mounted to inner frame structure 12 in two linear arrays at the top and the bottom of the housing. In addition, each conveyor chain 3 is partially wound about a further idler pulley 17" which serves to define horizontal chain portion 107.

Pulleys 17 of the lower rows are rotatably supported on opposite sides of an inner frame structure 12 by a bearing member 37 engineered to function as a chain tensioning device. Two long screws 38 on each side of frame structure 12 (FIGS. 3, 6, 8 and 9) push the bearing member down to tighten chains 3.

Frame structure 12 rests not on the bottom of housing 1 but is rather supported from the upper rim of the housing for facilitating adjustment of bevel gears 9 and 10 (FIG. 10). More particularly, frame 12 is secured to housing 1 via four alignment bolts 48 spaced around the perimeter of the upper rim of the housing. Aligning bolts 48 also aid in the alignment of cover 2 which is clamped to housing 1 by commercially available clamping levers 39 (see FIG. 10). Gaskets 40 and 40, are disposed between frame 12 and housing 1 and are made of graphite or other suitable insulating material.

As shown in FIG. 10, nitrogen container 18 is supported by brackets 41 from inner frame structure 12.

The process of depositing an ampule 16 into the cryogenic storage apparatus begins with the entry, into computer CC1 via keyboard 111, of a code number preassigned to the desired position of the ampule in the snaking array of support bars 4. Computer CC1 will compare the entered number with the numbers already in memory and verify the availability of the selected location. The code numbering system may simply take the form of a first set of consecutive numerals for successive bars 4 and a second set of consecutive numerals for adjacent ampule locations along a bar.

A tracking system is advantageously provided, exemplarily comprising computer CC1, together with an impulse module (not illustrated) on a driving shaft together with a decoder (not shown), both of which are commonly available. The decoder is operatively connected to computer CC1 for feeding thereto changes in the positions of endless conveyor chains 3, whereby the computer is at any time able to precisely locate the position of a given bar along path 103 within housing 1. Upon the selection of a particular ampule location (i.e., a specific bar 4 and a specific distance from one end of the bar), computer CC1 calculates the shortest direction of motion of chains 3 from the instantaneous position of the selected bar to access door 19 (FIG. 2) and will reverse the direction of chain drive, if necessary to minimize the search time.

Figure 11:
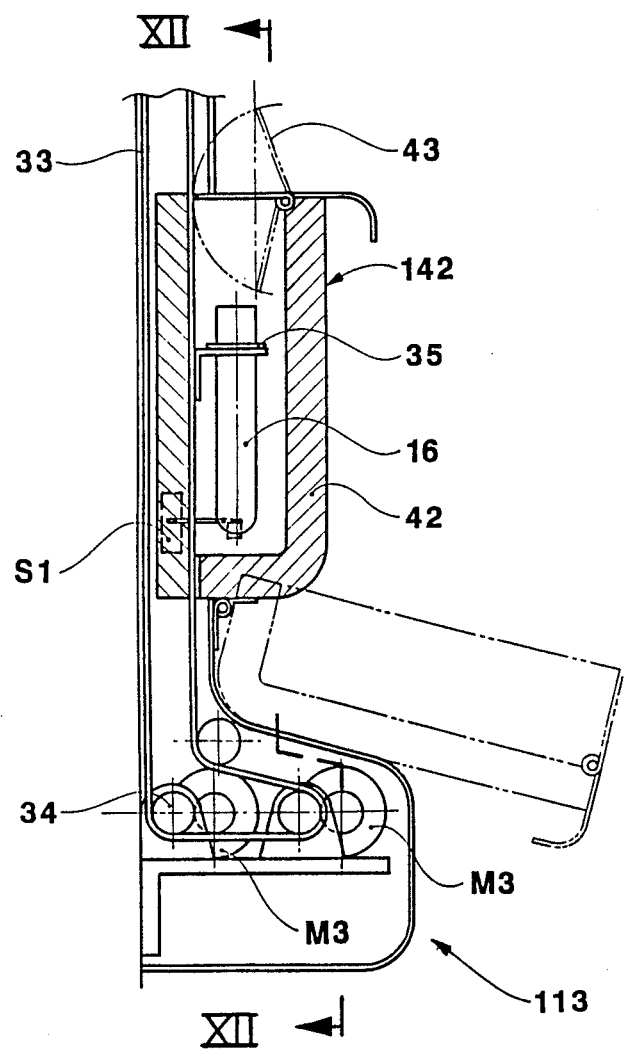
FIG. 11 is a partial cross-sectional view, on an enlarged scale, taken along line F—F in FIG. 1, depicting an intermediate storage container.
Figure 12:
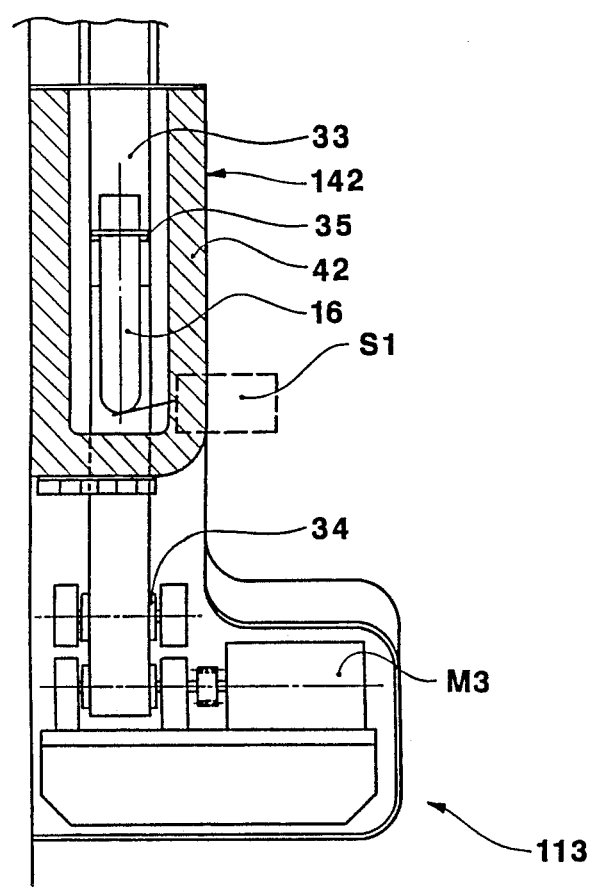
FIG. 12 is a partial cross-sectional view, on an enlarged scale, taken along line F—F in FIG. 11.

Further initial steps in the deposition of a specimen-containing ampule 16 in the cryogenic storage apparatus include the pivoting of an insulated cover member 42 of intermediate storage unit 142 from a closed position, illustrated in solid lines in FIG. 11, to an open position, shown in dot-dash lines. The ampule is then placed on a bracket member 35 attached to conveyor belt 33, cover member 42 being subsequently returned to the closed position. The ampule is now located temporarily inside a narrow insulated space of intermediate storage unit 142, enclosed by cover member 42 and by a spring loaded flap 43.

Upon placement of the ampule on bracket 35 (FIG. 11), a microswitch S1 signals computer CC1 that the ampule is ready to be deposited into the cryogenic storage apparatus. Computer activates lifting device 113 upon the arrival of the selected bar 4 precisely under door 19 which is closed at that stage of the ampule loading process. The activation of lifting device 113 consists in part of an energization of one of two motors M3 (see FIGS. 11 and 12) to drive conveyor belt 33 over pulleys 34 and thereby lift the ampule out from temporary storage inside intermediate storage unit 142 to a height determined by the location of a microswitch S7 (FIG. 3). Upon receiving a signal from microswitch S7, computer CC1 de-energizes the active motor M3, thereby halting the upward motion of the ampule.

While the ampule is being lifted from intermediate storage unit 142, ampule insertion and retrieval mechanism 50 is moved into a "zero" position, guided by dovetailed slide tracks 22 and 23 (FIG. 3) with a built-in gear track. Mechanism 50 is driven by a motor M1.

Motors M1, M2 and M4, switches S3, S4 and S6 and electromagnet 29 (FIG. 3) are supplied with power via a flat cable 49 (FIG. 1) extending from computer CC1 to ampule insertion and retrieval mechanism 50. Slide contacts 27 on a contact support 30 enable the transmission of electrical power to the motors, switches and electromagnet 29 of the ampule insertion and retrieval mechanism 50, even during rotation of an upper housing portion 25 thereof with respect to cover 2 of housing 1.

As illustrated in FIG. 3, electromagnet 29 is attached to a lower end of a spindle or rod 28 reciprocatingly driven by motor M4 via a belt 31 and grip rollers 44. Upon the reception of a signal from microswitch S7 and the subsequent arresting of conveyor belt 33, computer CC1 energizes motor M4 to shift rod 28 downwardly. Upon receiving a signal from microswitch S3, computer CC1 then deactivates motor M4, bringing the downward motion of rod 28 to a stop and energizes electromagnet 29 to form a magnetic link with a metal plate attached to the upper end of the ampule 16 held at the height of microswitch S7 by lifting device 113. The attachment of the metal plate on the ampule to the electromagnet closes a contact within the magnet, causing computer CC1 to again energize motor M4, this time in the reverse direction, to lift rod 28, together with the attached ampule. Upward motion of rod 28 is stopped by computer CC1 upon the reception thereby of a signal from microswitch S4.

As further depicted in FIG. 3, small magnets 32 are recessed into dovetailed side track or rail member 23 precisely at the location of the ampules on bars 4 within housing 1. Depending on the designated location at which the ampule carried by insertion and retrieval mechanism 50 is to be placed, microswitch S2 induces comuter CC1 to stop motor M1 and to activate two motors M5 (each of which is a member of a pair, an active motor and a backup). The activated motors M5 are located at opposite ends of access door 19, which extends substantially across the width of cover 2.

Motors M5 rotate respective pinions 21 which in turn translate respective racks 20 secured to door 19, whereby door 19 slides along a sloped surface 119 (FIG. 3) of cover 2 and opens access to the interior of housing 1. Door 19 is pushed against sloped surface 119 by rollers 45 which apply a torque to racks 20 and, consequently, wedge-shaped door 119 under the action of a lever arm 46 and an adjustable weight 47. Door 19 is self-aligning and self-sealing due to its-wedge-shaped cross section.

After microswitch S5 of the door opening and closing mechanism signals computer CC1 that door 19 has been opened, the computer stops motor M5 and also cause motor M2 of insertion and retrieval mechanism 50 to rotate upper housing portion 25 of the insertion and retrieval mechanism 180° around with the help of a ring gear which is part of dovetailed sliding carriage 21.

Two projecting pins 26 (FIGS. 3 and 5) connected to an inner surface of upper housing portion 25 of insertion and retrieval mechanism 50 cooperate with a microswitch S6 mounted to a sliding carriage member 24 of the insertion and retrieval mechanism to signal computer CC1 that rotation of 180° has been accomplished. The computer then deactivates motor M2 and simultaneously energizes motor M4 to lower rod 28, together with the ampule through the opened access door 19 and into the cooling chamber of the cryogenic storage apparatus.

Upon removal of an ampule from the cryogenic storage apparatus, a laser reader reads a bar code attached to the removed ampule to verify that the correct ampule has been retrieved. In the absence of verification, the retrieved ampule is returned immediately to housing 1 and an alarm signal is generated for alerting an operator as to the error. In addition, or alternatively, an alphanumeric code identifying the retrieved ampule may be displayed on a monitor connected to computer CC1. If verification occurs, the removal of the ampule proceeds normally.

Microswitch S3 then induces computer CC1 to stop motor M4 and the downward motion of rod 28 and to de-activate electromagnet 29, thereby enabling the deposition of the ampule into an aperture in the selected bar 4 at the selected position therealong. Opened contacts within electromagnet 29 then cause computer CC1 to lift rod 28 out of the housing through door 19. A subsequent signal from microswitch S4 leads to the arresting of the upward motion of the rod and causes computer CC1 to activate motors M5 to close door 19 and motor M6 to recommence continuous motion of bars 4 and their ampules 16 along path 103 through housing 1.

Figure 4:
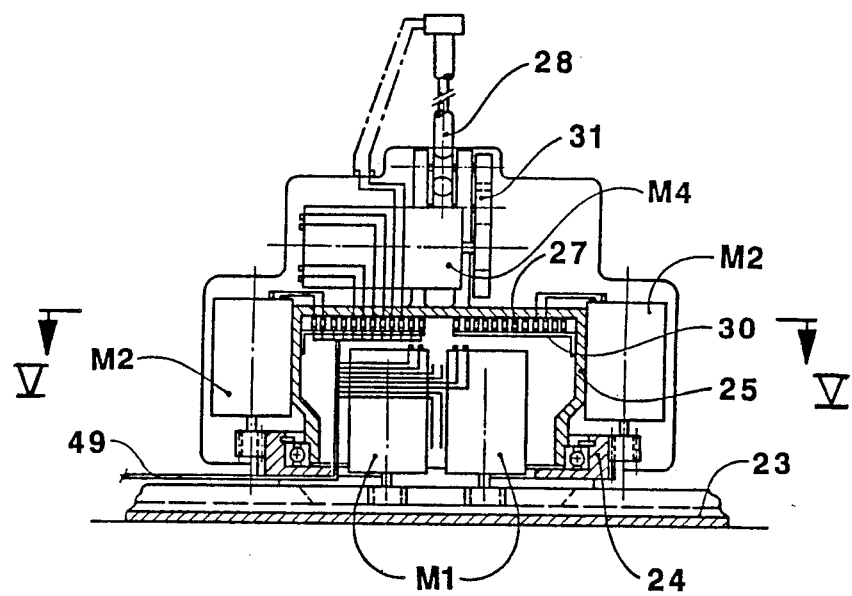
FIG. 4 is a partial cross-sectional view taken along line B—B in FIG. 3, showing a lifting mechanism.

As shown in detail in FIGS. 3 and 4, insertion and retrieval mechanism 50 includes dovetailed rail member 24 which is operatively fastened to cover 2 of housing 1 and extends parallel to door 19. Carriage 24 is slidably mounted to rail member 24 for motion therealong. Motor M1 (or its normally inactive backup) serves to move the carriage 24 along rail member 24 via a rack and pinion transmission assembly. Under the control of computer CC1, electromagnet 29 is raised and lowered by rod 28 to secure a hold on a selected ampule 16 positioned in housing 1 in juxtaposition to door 19.

Motors M4 serve to move rod 28 and electromagnet 29 a linear path through door 19. Upper housing portion 25 is rotatably mounted to carriage member 24, while motors M4 are mounted to housing portion 25. Rotary drive motors M2 (FIG. 4) are operatively connected to the rotatable housing portion for rotating the same relative to carriage member 24.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A cryogenic storage apparatus comprising:
   housing means for defining a storage chamber and for containing a cooling fluid, said housing means having an access door;
   drive means operatively connected to said door for alternately opening and closing same;
   holder means in said chamber for supporting a plurality of specimen-containing receptacles;
   conveyor means for moving said holder means, together with said plurality of receptacles, through said fluid in said chamber along a path including a snaking portion, said snaking portion having a plurality of vertically extending folds, said path including a segment juxtaposed to said door;
   cooling means at least partially in said chamber for maintaining said chamber at a predetermined low temperature;
   tracking means operatively connected to said conveyor means for automatically tracking the positions of said plurality of receptacles during motion thereof along said path under action of said conveyor means;
   extraction means disposed outside of said housing means at said door for removing a selectable one of said receptacles positioned in said chamber in juxtaposition to said door;
   selection means outside of said housing means for enabling a selection of one of said receptacles by an operator; and
   control means operatively connected to said selection means, said tracking means, said drive means, said conveyor means and said extraction means for operating said conveyor means, upon selection of a given one of said receptacles via said selection means, to move said given one of said receptacles along said path to said door, for operating said drive means to open said door, for operating said extraction means to remove said given one of said receptacles from said holder means and out through the opened door.

2. The apparatus defined in claim 1 wherein said extraction means includes:
   a carriage member operatively mounted to said housing means for motion in a direction extending substantially parallel to said door;
   first linear drive means for moving said carriage member;
   holding means for securing a hold on a selected one of said receptacles positioned in said chamber in juxtaposition to said door;

second linear drive means connected to said holding means for moving said holding means along a substantially linear path through said door upon an opening thereof;

a housing portion rotatably mounted to said carriage member, said second linear drive means being at least partially mounted to said housing; and rotary drive means operatively connected to said housing portion for rotating same relative to said carriage member.

3. The apparatus defined in claim 1 wherein said door has a wedge-shaped cross-section.

4. The apparatus defined in claim 3 wherein said door engages a sloped surface of said housing means, said means for alternately opening and closing said door including means for sliding said door along said surface.

5. The apparatus defined in claim 1 wherein said conveyor means includes a pair of flexible endless elements extending along said path, said holder means including a plurality of bar members pivotably connected to and extending between said endless elements.

6. The apparatus defined in claim 1 wherein said cooling means includes a coolant container having at least a portion with a substantially L-shaped cross-section with a pair of hollow substantially planar leg members extending orthogonally with respect to one another, one of said leg members extending horizontally and proximately to an upper wall of said housing means and another of said leg members extending vertically and proximately to a side wall of said housing means.

7. The apparatus defined in claim 6 wherein said other of said leg members is formed with cooling fins.

8. The apparatus defined in claim 7 wherein said cooling fins are disposed between said other of said leg members and said side wall.

9. The apparatus defined in claim 6 wherein said one of said leg members has an open upper side.

10. The apparatus defined in claim 1 wherein said control means comprises a computer.

11. A cryogenic storage apparatus comprising:

housing means for defining a storage chamber and for containing a cooling fluid, said housing means having an access door;

means operatively connected to said door for alternately opening and closing same;

holder means in said chamber for supporting a plurality of specimen-containing receptacles;

conveyor means for moving said holder means, together with said plurality of receptacles, through said fluid in said chamber along a path including a snaking portion, said path including a segment juxtaposed to said door;

cooling means at least partially in said chamber for maintaining said cooling fluid at a predetermined low temperature; and extraction means disposed outside of said housing means at said door for removing a selectable one of said receptacles positioned in said chamber in juxtaposition to said door.

12. The apparatus defined in claim 11 wherein said snaking portion has a plurality of vertically extending folds.

13. The apparatus defined in claim 11 wherein said extraction means includes:

a carriage member operatively mounted to said housing means for motion in a direction extending substantially parallel to said door;

first linear drive means for moving said carriage member in said direction;

holding means for securing a hold on a selected one of said receptacles positioned in said chamber in juxtaposition to said door;

second linear drive means connected to said holding means for moving said holding means along a substantially linear path through said door;

a housing portion rotatably mounted to said carriage member, said second linear drive means being at least partially mounted to said housing; and rotary drive means operatively connected to said housing portion for rotating same relative to said carriage member.

14. The apparatus defined in claim 11 wherein said cooling means includes a coolant container having at least a portion with a substantially L-shaped cross-section with a pair of hollow substantially planar leg members extending orthogonally with respect to one another, one of said leg members extending horizontally and proximately to an upper wall of said housing means and another of said leg members extending vertically and proximately to a side wall of said housing means.

15. The apparatus defined in claim 14 wherein said one of said leg members has an open upper side.

16. The apparatus defined in claim 11, further comprising:

tracking means operatively connected to said conveyor means for automatically tracking the positions of said plurality of receptacles during motion thereof along said path under action of said conveyor means;

selection means outside of said housing means for enabling a selection of one of said receptacles by an operator; and control means operatively connected to said selection means, said tracking means, said drive means, said conveyor means and said extraction means for operating said conveyor means, upon selection of a given one of said receptacles via said selection means, to move a said given one of said receptacles along said path to said door, for operating said drive means to open said door, for operating said extraction means to remove said given one of said receptacles from said holder means and out through the opened door.

17. The apparatus defined in claim 11 wherein said control means comprises a computer.

18. A cryogenic storage apparatus comprising:

housing means for defining a storage chamber and for containing a cooling fluid, said housing having an access door;

drive means operatively connected to said door for alternately opening and closing same;

holder means in said chamber for supporting a plurality of specimen-containing receptacles;

conveyor means for moving said holder means, together with said plurality of receptacles, along a path through said fluid in said chamber, said path including a segment juxtaposed to said door;

cooling means at least partially in said chamber for maintaining said chamber at a predetermined low temperature;

tracking means operatively connected to said conveyor mean for automatically tracking the positions of said plurality of receptacles during motion thereof along said path in response to said conveyor means;

extraction means disposed outside of said housing means at said door for removing a selectable on of said receptacles positioned in said chamber in juxtaposition to said door;

control means operatively connected to said tracking means, said drive means, said conveyor means and said extraction means for operating said conveyor means to move a given one of said receptacles along said path to said door, for operating said drive means to open said door, and for operating said extraction means to remove said given one of said receptacles from said holder means and out through the opened door.

19. The apparatus defined in claim 18 wherein said control means and said housing means are disposed at least in part at the same location.

20. The apparatus defined in claim 18, further comprising selection means outside of said housing means for enabling a selection of one of said receptacles by an operator, said control means being operatively connected to said selection means for operating said conveyor means, said drive means and said extraction means upon selection of one of said receptacles via said selection means.

21. The apparatus defined in claim 18 wherein said cooling means includes a coolant container having at least a portion with a substantially L-shaped cross-section with a pair of hollow substantially planar leg members extending orthogonally with respect to one another, one of said leg members extending horizontally and proximately to an upper wall of said housing means and another of said leg members extending vertically and proximately to a side wall of said housing means.

22. The apparatus defined in claim 21 wherein said one of said leg members has an open upper side.

23. A cryogenic storage apparatus comprising:
housing means for defining a storage chamber and for containing a cooling fluid, said housing means having an access door;
means operatively connected to said door for alternately opening and closing same;
holder means in said chamber for supporting a plurality of specimen-containing receptacles;
conveyor means for moving said holder means, together with said plurality of receptacles, along a path through said fluid in said chamber, said path including a segment juxtaposed to said door;
cooling means at least partially in said chamber for maintaining said cooling fluid at a predetermined low temperature, said cooling means including a coolant container having at least a portion with a substantially L-shaped cross-section with a pair of hollow substantially planar leg members extending orthogonally with respect to one another, one of said leg members extending horizontally and proximately to an upper wall of said housing means and another of said leg members extending vertically and proximately to a side wall of said housing means; and
extraction means disposed outside of said housing means at said door for removing a selectable one of said receptacles positioned in said chamber in juxtaposition to said door.

24. The apparatus defined in claim 23 wherein said one of said leg members has an open upper side.

25. The apparatus defined in claim 24 wherein said other of said leg members is formed with cooling fins.

26. The apparatus defined in claim 25 wherein said cooling fins are disposed between said other of said leg members and said side wall.

27. A cryogenic storage apparatus comprising:
housing means for defining a storage chamber and for containing a cooling fluid, said housing means having an access door;
means operatively connected to said door for alternately opening and closing same;
holder means in said chamber for supporting a plurality of specimen-containing receptacles;
conveyor means for moving said holder means, together with said plurality of receptacles, along a path through said fluid in said chamber, said path including a segment juxtaposed to said door;
cooling means at least partially in said chamber for maintaining said cooling fluid at a predetermined low temperature;
an insulated enclosure outside of said housing means; and
extraction means disposed outside of said housing means at said door for removing a selectable one of said receptacles positioned in said chamber in juxtaposition to said door and inserting the removed one of said receptacles into said enclosure.

28. The apparatus defined in claim 27 wherein said enclosure is attached to said housing means.

29. A cryogenic storage apparatus comprising:
housing means for defining a storage chamber and for containing a cooling fluid, said housing means having an access door;
door shifting means operatively connected to said door for alternately opening and closing same;
holder means in said chamber for supporting a plurality of specimen-containing receptacles;
conveyor means for moving said holder means, together with said plurality of receptacles, through said fluid in said chamber along a cooling path including a segment juxtaposed to said door;
cooling means at least partially in said chamber for maintaining said cooling fluid at a predetermined low temperature; and
a receptacle extraction mechanism disposed outside of said housing means at said door, said extraction mechanism including:
a carriage member operatively mounted to said housing means for motion in a direction extending substantially parallel to said door;
first linear drive means for moving said carriage member in said direction;
holding means for securing a hold on a selected one of said receptacles positioned in said chamber in juxtaposition to said door;
second linear drive means connected to said holding means for moving said holding means along a substantially linear path through said door;
a housing portion rotatably mounted to said carriage member, said second linear drive means being at least partially mounted to said housing; and
rotary drive means operatively connected to said housing portion for rotating same relative to said carriage member.

30. The apparatus defined in claim 29 wherein said path includes a snaking portion having a plurality of vertically extending folds.

31. The apparatus defined in claim 29, further comprising an insulated enclosure outside of said housing means, said extraction means being operative to transfer said receptacles between said housing means and said insulated enclosure.

32. The apparatus defined in claim 29, further comprising:

tracking means operatively connected to said conveyor means for automatically tracking the positions of said plurality of receptacles during motion thereof along said path in response to said conveyor means; and control means, operatively connected to said tracking means, said first linear drive means, said second linear drive means, said rotary drive means, said conveyor means and said door shifting means, for operating said conveyor means to move a given one of said receptacles along said path to said door, for operating said door shifting means to open said door, and for operating said extraction means to remove said given one of said receptacles from said holder means and out through the opened door.

33. A cryogenic storage apparatus comprising:

housing means for defining a storage chamber and for containing a cooling fluid, said housing means having an access door;

door shifting means operatively connected to said door for alternately opening and closing same;

holder means in said chamber for supporting a plurality of specimen-containing receptacles;

conveyor means for moving said holder means, together with said plurality of receptacles, through said fluid in said chamber along a cooling path including a segment juxtaposed to said door;

cooling means at least partially in said chamber for maintaining said cooling fluid at a predetermined low temperature;

extraction means disposed outside of said housing means at said door for removing a selectable one of said receptacles positioned in said chamber in juxtaposition to said door; and verification means at said door for automatically verifying that the correct receptacle has been retrieved by said extraction means.

34. The apparatus defined in claim 33, wherein said verification means includes a laser reader for scanning bar codes attached to said receptacles.

* * * * *